(12) United States Patent
Grandt et al.

(10) Patent No.: US 9,408,947 B2
(45) Date of Patent: Aug. 9, 2016

(54) NON-METALLIC TUBES FOR MEDICAL DEVICES

(75) Inventors: Axel Grandt, Strassberg (DE); Andrew Jeffrey, Hythe (GB)

(73) Assignee: ABBOTT LABORATORIES VASCULAR ENTERPRISES LIMITED, Dublin (IE)

(*) Notice: Subject to any disclaimer, the term of this patent is extended or adjusted under 35 U.S.C. 154(b) by 971 days.

(21) Appl. No.: 13/386,886

(22) PCT Filed: Jul. 30, 2010

(86) PCT No.: PCT/EP2010/004678
§ 371 (c)(1),
(2), (4) Date: May 3, 2012

(87) PCT Pub. No.: WO2011/012314
PCT Pub. Date: Feb. 3, 2011

(65) Prior Publication Data
US 2012/0310180 A1   Dec. 6, 2012

(30) Foreign Application Priority Data
Jul. 31, 2009 (EP) .................................. 09009923

(51) Int. Cl.
*A61L 29/12* (2006.01)
*A61L 29/18* (2006.01)

(52) U.S. Cl.
CPC ............... *A61L 29/126* (2013.01); *A61L 29/18* (2013.01)

(58) Field of Classification Search
CPC ................ A61M 25/0045; A61M 2025/0042; A61M 2025/0047; A61M 2025/0046; A61M 25/005; A61L 29/18; A61L 29/126

USPC ............................... 604/264, 523, 524, 93.01
See application file for complete search history.

(56) References Cited

U.S. PATENT DOCUMENTS

| | | | |
|---|---|---|---|
| 4,909,796 A | 3/1990 | Hagio et al. | |
| 5,378,237 A | 1/1995 | Boussignac et al. | |
| 6,325,780 B1 | 12/2001 | Schaible et al. | |
| 2002/0146557 A1 | 10/2002 | Claude et al. | |
| 2004/0078052 A1* | 4/2004 | St. Pierre et al. | 606/194 |
| 2004/0082965 A1* | 4/2004 | Beckham | 606/192 |
| 2008/0103444 A1* | 5/2008 | Jimenez | 604/103.09 |
| 2009/0165881 A1* | 7/2009 | Tegg et al. | 138/137 |

FOREIGN PATENT DOCUMENTS

| | | |
|---|---|---|
| EP | 1 388 346 | 2/2004 |
| WO | WO 03/000307 | 1/2003 |

OTHER PUBLICATIONS

Celsite Ports with Anthron Catheters Product Information, RAFI International, Retrieved Aug. 3, 2012, http://www.rafi.ro/fisiere_produse/66.pdf.
RAUMEDIC—micro-extrusion from high-temperature thermoplastics brochure, RAUMEDIC AG, Germany. Retrieved Aug. 3, 2012. URL: http://www.raumedic.de/fileadmin/user_upload/service/en/RAUMEDIC_micro-extrusion.pdf.

* cited by examiner

*Primary Examiner* — Kami A Bosworth
*Assistant Examiner* — Hamza Darb
(74) *Attorney, Agent, or Firm* — Workman Nydegger; John Kwok

(57) ABSTRACT

The present invention refers to medical devices comprising a non-metallic micro tube containing FRP (fiber reinforced polymer), especially to respective tubings, used for constructing catheters like balloon dilation catheters, stent delivery catheters, guiding catheters and diagnostic catheters.

9 Claims, 2 Drawing Sheets

NON-METALLIC TUBES FOR MEDICAL DEVICES

CROSS REFERENCE TO RELATED APPLICATIONS

This application is a U.S. Nationalization of PCT Application Number PCT/EP2010/004678, filed on Jul. 30, 2010, which claims priority to European Patent Application No. 09009923.5, filed on Jul. 31, 2009, the entireties of which are incorporated herein by reference.

FIELD OF THE INVENTION

The present invention refers to medical devices comprising a non-metallic micro tube containing FRP (fiber reinforced polymer), especially to respective tubings, used for constructing catheters like balloon dilation catheters, stent delivery catheters, guiding catheters and diagnostic catheters.

BACKGROUND OF THE INVENTION

Angioplasty is an efficient and successful method of opening stenosis in the vascular system. In a popular form of angioplasty, a balloon catheter is advanced through the vascular system until the balloon, which is carried at the distal end of a catheter shaft, and which may carry an expandable stent, is positioned across the stenosis or damaged vessel. By inflating the balloon pressure is applied to the obstruction, which is moved by pressing it against the inner wall of the vessel, whereby the vessel is opened for improved flow. Due to the expansion of the balloon, the stent, which—if used—is situated on the balloon, is also expanded for aiding in repairing the vessel wall and hindering obstruction. As a last step the stent is then released by deflating the balloon reducing its circumference until refolding of the balloon occurs followed by removal of the balloon and catheter from the vessel along a guide wire.

There are various types of balloon catheters. One type is fed over a guide wire (i.e., "over-the-wire" catheters) and another type serves as its own guide wire ("fixed-wire" catheters). There have been developments of variations of these two basic types: the so-called "rapid exchange" type, "innerless" catheters, and others.

In another popular form of angioplastie selfexpanding stents are delivered to the target site in a vessel via a self-expanding stent delivery catheter. Usually the stent is covered by a sheath to keep it in the contracted configuration on the catheter until it reaches the target side. The sheath is then retracted in order to release the stent and the catheter is subsequently removed from the vessel.

If a catheter, like a balloon catheter, is used in percutaneous transluminal angioplasty (PTA) or percutaneous transluminal coronary angioplasty (PTCA), it is typically advanced through a guide catheter to a preselected vessel location, such as the aorta, for example. Using an imaging technique like fluoroscopy or MRI, the surgeon advances the catheter until the balloon is located across the stenosis or obstruction. This may involve the use of a guide wire over which the catheter is moved or alternatively the catheter may act as its own guide wire. Besides the fact that a smooth advancement in the vessels is in itself very advantageously, a possible origin of trouble arriving from this advancement of the catheter is the friction between the wire and the inner lumen of the catheter when guiding the catheter along the wire. As the movement in the vessels is highly difficult and a task requiring great handling skills any resistance in addition to those unavoidable due to the nature of the vessels being penetrated is strictly unwanted. Accordingly besides smoothness of the catheter (tip) itself a smooth movement of the wire inside the catheter avoiding as much friction as possible is highly desired. However, on the other hand the catheter needs sufficient pushability in order to advance the catheter over for example a stenosis in the vessel.

In order to address these conflictive needs, high flexibility and high pushability, many catheters, in particular PTA or PTCA catheters include a proximal portion that is relatively stiff, conventionally made from a stainless steel hypotube and a transition to a relatively soft and flexible distal portion of the catheter conventionally made from polymeric materials like PEBAX or Nylon.

Further, diagnostic catheters which are commonly used to facilitate the diagnosis of vascular diseases such as coronary artery disease and peripheral vascular disease and guide catheters which are commonly used to facilitate advancement of a PTA or PTCA catheter to the treatment site within the vessel when treating vascular diseases, commonly include a metallic braid reinforcement layer disposed between an inner layer and an outer layer. The braid reinforcement provides torsional rigidity, column strength, kink resistance, as well as radiopacity and is conventionally made from stainless steel wire.

However, a major drawback of these conventional braid reinforcement materials and hypotube materials such as stainless steel is their incompatibility with MRI (magnetic resonance imaging) due to their ferro-magnetic properties. MRI has become a standard in non-invasive diagnostic imaging and it is expected that MRI will be used in the future also for endovascular diagnosis and even treatment. The benefit for the patient compared to currently used x-ray angiogram is the absence of $\gamma$ ray exposure and the use of less impacting contrast media.

Therefore, there is a clear need for improved high strength materials especially tubes for medical devices that allow use of these medical devices for effective treatment of the patient. There is a strong need for biocompatible and MRI compatible materials providing sufficient strength and elasticity.

SUMMARY OF THE INVENTION

The present invention provides medical devices comprising a non-metallic micro tube containing FRP (Fiber Reinforced Polymer) or continuous-fiber-reinforced implantable-grade polymer. The present invention particularly refers to MRI compatible tubings, used for constructing catheters like balloon dilation catheters, stent delivery catheters, guiding catheters and diagnostic catheters. Just as a clarification it should be made clear that this said micro tube is not meant to be a balloon or an inflatable member and thus is non-inflatable.

The invention further provides dual layer, trilayer or multilayer non-metallic micro tubes and methods for production thereof. In one embodiment the non-metallic microtube comprises PEEK (Polyetheretherketone) Polymer and Fiber Reinforced Polymer (FRP) containing continuous reinforced fiber material. The polymer used for at least one of the FRPs may be a thermoplastic or thermoset polymeric material.

In another embodiment of the present invention the non-metallic microtube comprises Fiber Reinforced PEEK (Polyetheretherketone) Polymer In one embodiment of the present invention the non-metallic microtube further comprises polytetrafluoroethylene (PTFE) Teflon.

In a further embodiment the non-metallic microtube comprises PEEK, FRP, and PTFE.

These non-metallic microtubes according to the present invention can be used for a catheter shafts or other tubular catheter components and compare favorably with metallic alternatives. The mechanical properties of these continuous reinforced micro tubes are comparable to those of metallic materials of a similar dimension and outline while still having the advantage of their respective basic polymer.

DETAILED DESCRIPTION

Figure 1:
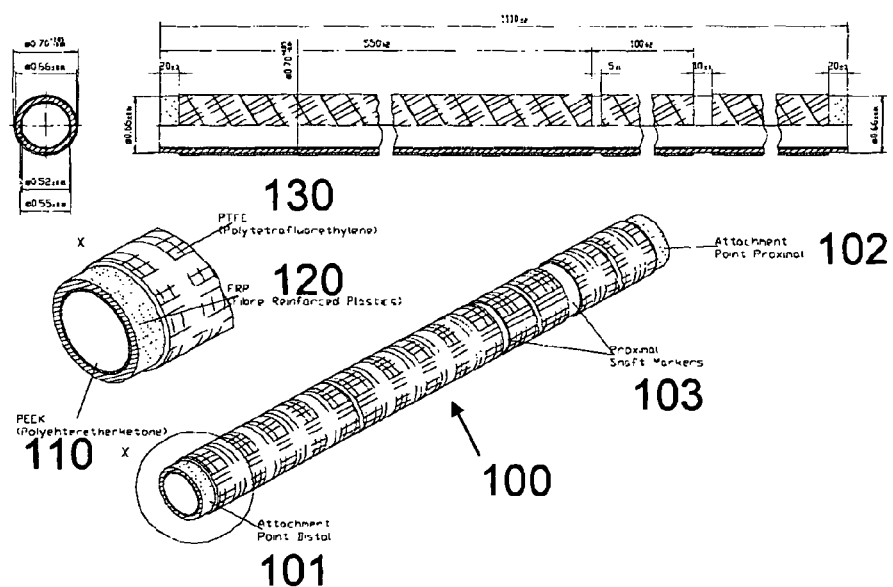
FIG. 1 is a view of a non-metallic trilayered microtube according to the invention.

The present invention provides medical devices comprising a non-metallic micro tube containing continuous-fiber-reinforced implantable-grade polymer. The present invention particularly refers to MRI compatible tubings, used for constructing catheters like balloon dilation catheters, stent delivery catheters, guiding catheters and diagnostic catheters. As said above and as a major embodiment said micro tube (non-metallic micro tube) is neither a balloon nor an inflatable member and thus is non-inflatable.

The present invention is directed to a medical device comprising a non-metallic microtube, the non-metallic microtube comprising FRP (Fiber Reinforced Polymers). Usually, and as the major embodiment the invention is thus also directed to a medical device comprising a non-metallic, non-inflatable microtube, the non-metallic, non-inflatable microtube comprising FRP (Fiber Reinforced Polymers).

In one embodiment, the non-metallic microtube comprising FRP are MRI compatible tubings.

In one embodiment the medical devices are MRI compatible medical devices. The medical devices particularly include catheters like balloon dilatation catheters, stent delivery catheters, guiding catheters and diagnostic catheters.

FRP (Fiber Reinforced Polymers) are defined as a polymeric material in which fibers or fiber filaments, selected from long or short, non-continuous or continuos fibers, are embedded reinforcing the polymer, especially an implantable-grade polymer. Examples could include fiber glass (glass reinforced polymer) or especially CRP (Carbon Reinforced Polymer or Carbon fiber Reinforced Polymer) (see below). FRPs are typically organized in a laminate structure, embedded within a thin layer of light polymer matrix material. The fibres provide the strength and stiffness, while the polymer binds and protects the fibers from damage, and transfers the stresses between fibers.

The embedded fibers or fiber filaments in the FRPs of the microtubes of the medical devices according to the present invention are derived from natural sources or preferably are synthetic material. Non-limiting examples include aramid, boron, glass (fiberglass) or carbon fibers; or also carbon-fiber and PEEK combined to form single filaments. Possibly the fibers are mixed with one another or with Kevlar or Aluminium fibers which could possibly also be used alone. If in a preferred embodiment carbon fibers are used the FRP is then called CRP (Carbon Reinforced Polymer or Carbon fiber Reinforced Polymer). Carbon (fiber) reinforced polymer is a fiber reinforced polymer in which the polymer is as non-limiting examples selected from epoxy, or other polymers, such as polyester, vinyl ester or nylon; preferably epoxy.

All the different fibers mentioned above can be applied as single or multiple elements, alone or in combinations of any or all of the above mentioned fibers depending on the application of specific requirements for the medical device.

In a preferred embodiment, the embedded fiber filaments consist of carbon fibers, or carbon fiber and PEEK are combined to form single filaments.

The polymeric material of the FRPs of the micro tubes of the medical devices according to the present invention used are including Polyester, Epoxy or Nylon or especially PEEK or (other) (suitable) pseudo-thermoplastic.

The polymers used for the microtubes of the medical devices according to the present invention are standard polymers preferably suitable for medical devices. Non-limiting examples include Polyester, Epoxy, Vinyl Ester or Nylon or especially PEEK or (other) pseudo-thermoplastic. Suitable pseudo-thermoplastics are pseudo-thermoplastics which have a high thermal index and whose properties can be maintained during a continuous service temperature of 450° F. (232° C.) or for short excursions as high as 900° F. (482° C.). Non limiting examples of suitable pseudo-thermoplastics are polyimides or loaded polyimides such as e.g. carbon loaded polyimide; or include Polyetheretherketone—PEEK, ENSIFONE® PSU (Polysulfonel, RILSAN®AESNO Nylon 12, TROGAMID®, CELAZOLE® PBI—[meltprocessable grades], Ultem 1000 polyetherimide (PEI) or others. Generally these polymers are rigid, high-strength, semi-tough thermoplastics that have high heat deflection temperatures and maintain their mechanical properties over a wide temperature range.

In a further embodiment the non-metallic microtube comprises fiber reinforced PEEK or fiber-reinforced pseudothermoplastic, most preferably carbo-fiber reinforced PEEK as FRP.

In one embodiment the non-metallic microtube comprises pseudothermoplastic, especially polyimide, preferably fiber-reinforced polyimide.

The non-metallic tube according to the present invention further may comprise PTFE.

In one embodiment of the present invention the fibers of the FRP are embedded in a preferential direction or preferential directions or orientation. In one embodiment the fibers in at least one FRP comprised in a non-metallic hypotube are directionally orientated, with "directionally orientated" meaning that the fibers in the FRP are embedded in a preferential direction or—if there are more than one layer of fibers—in preferential directions or orientations while each single layer still has the fibers unidirectionally orientated. In one embodiment the fibers of an FRP comprised in a non-metallic hypotube are unidirectionally orientated. In another embodiment, the non-metallic hypotube comprises a first layer of FRP which has unidirectionally orientated fibers in a first direction and a second layer of FRP which has unidirectionally orientated fibers in a second direction. By embedding the fibers or fiber filaments preferentially unidirectionally aligned into the microtube the heterogeneous materials are no longer isotropic but have preferential directions depending on the orientation of the fibers.

In one embodiment of the present invention the non-metallic microtube of the medical device has two—preferably different—layers of polymeric material, i.e. is dual layered, or has at least two layers of polymeric material or has optionally three or more layers of polymeric material.

In one preferred embodiment the medical device comprises a non-metallic microtube that has two layers, wherein the inner layer of the microtube is made from fiber reinforced PEEK or a pseudothermoplastic and the outer layer is made from PTFE.

In another preferred embodiment of the present invention the medical device comprises a non-metallic microtube that has three—preferably different—layers of polymeric material, i.e. is trilayered. In one preferred embodiment the inner layer of the microtube is made from PEEK or a pseudothermoplastic, the intermediate layer is made from FRP and the outer layer is made from PTFE. In this embodiment the intermediate layer is preferably made from carbon reinforced polymer (CRP).

In further embodiments of the present invention the non-metallic tube may further comprise an outer layer comprising a functional coating to act as a biointerface and aid blood-foreign material interaction between the device and the blood fluid contact surface, or form a lubricious barrier to aid movement through the conduits of the vasculature.

Figure 2:
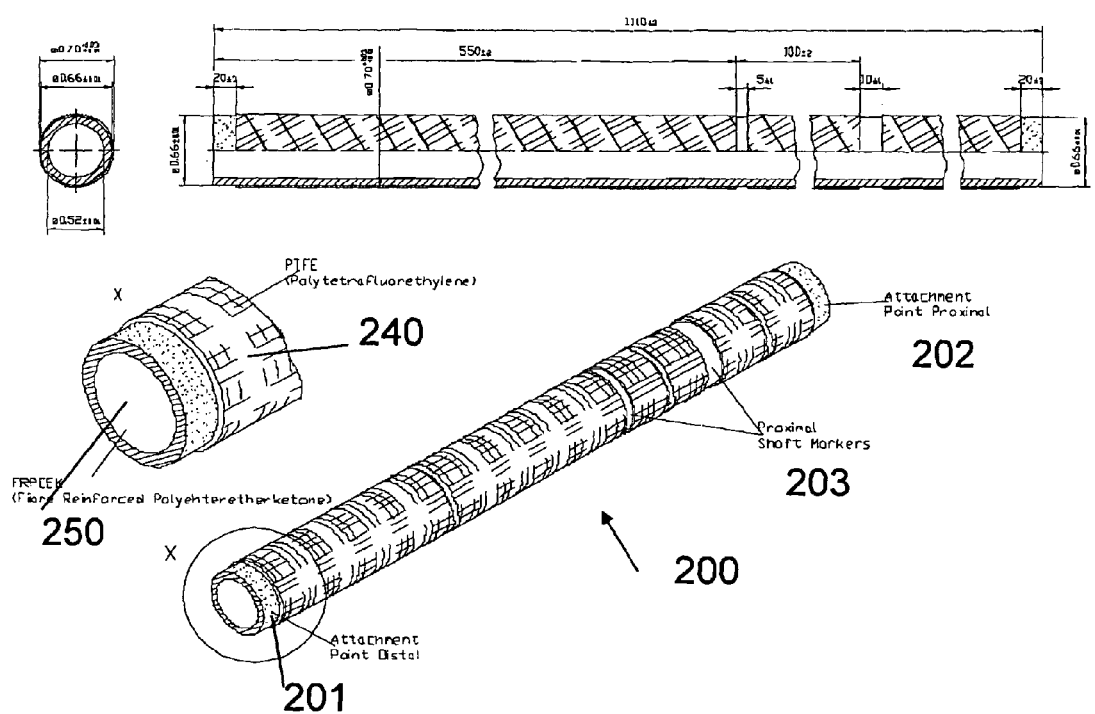
FIG. 2 is a view of a non-metallic duallayered microtube according to the invention.

Referring now to the embodiments depicted in FIGS. 1 and 2 there are shown two non-metallic micro tubes, a trilayered and a duallayered microtube according to the present invention.

In one embodiment as depicted in FIG. 1 the non-metallic microtube may consist of a tri-layer design comprising an inner core of polymer made from for example but not limited to PEEK (Polyetheretherketone), a mid layer of FRP—(Fiber Reinforced Polymer)—continuous reinforced fiber filaments which are embedded into a polymer matrix preferably in a preferential direction or orientation, and an outer or top layer consisting of material providing a low coefficient of friction for example but not limited to Teflon polytetrafluoroethylene (PTFE).

In a preferred embodiment of the present invention the non-metallic microtube has an inner layer made of PEEK, and an intermediate layer made of a tube made from CRP (Carbon Reinforced Polymer) with the fiber filaments in a preferential direction or orientation which is coated on its outside with Teflon polytetrafluoroethylene (PTFE) to result in the outer layer.

In an alternative embodiment of the present invention as depicted in FIG. 2 the non-metallic microtube is a bi-layer or duallayer design with an inner core made of for example but not limitation PEEK with continuous reinforced fiber filaments embedded directly in the PEEK polymer matrix in a preferential direction or orientation, and an outer top layer of material providing a low coefficient of friction for example but not limitation Teflon polytetrafluoroethylene (PTFE).

The present invention is further directed to methods of manufacturing medical devices comprising non-metallic microtubes, the method comprising the steps of a) extruding a first material over a mandrel to form the inner layer; b) applying a second material over the first material. As said above and as a major embodiment said micro tube is neither a balloon nor an inflatable member and thus is non-inflatable. Accordingly—usually and as the major embodiment—these methods of manufacturing medical devices comprising non-metallic, non-inflatable microtubes comprise the steps of a) extruding a first material over a mandrel to form the inner layer; b) applying a second material over the first material.

In one embodiment of the present invention the method for manufacture further comprises the step of c) subjecting the outer surface of the inner layer to a surface treatment before application of the second material.

In a preferred embodiment of the present invention the method for manufacture further comprises the step of d) precision grinding of the dual layer tube.

In yet a preferred embodiment the method for manufacture further comprises the step of e) applying a third material over the second material.

The multi layer non-metallic micro tube according to the present invention may be processed using conventional and understood thermoplastic processing equipment and techniques such as for example but not limitation injection molding, extrusion, pultrusion, compression molding, powder coating, spraying and dip coating.

Referring now back to FIG. 1 depicting a trilayered microtube 100 according to the present invention. It is shown a preferred embodiment of a tri-layer micro tube construction utilizing a PEEK inner layer 110 a carbon reinforced polymer mid layer 120 and Polytetrafluorethylene (PTFE) outer layer 130.

FIG. 2 on the other hand illustrates a duallayered microtube 200 according to the present invention, the micro tube construction utilizing the fiber reinforced Polyetheretherketone base layer 240 with Polytetrafluorethylene outer layer 250.

In one embodiment of the present invention represented in FIG. 1 the inner layer 110 of the microtube 100 is made of a commercially available thermoplastic polymer such as PEEK that can be produced in ultra thin walled dimensions. PEEK has a high thermal index or continuous service temperature of 500° F./260° C. or even higher for PEEK-HT™. Also PEEK is commercially available in highly biocompatible grades. The inner layer forming thermoplastic polymer is extruded over a mandrel like e.g. a copper coated wire thereby stabilizing the tube during further processing and preventing a collapse of the core lumen.

In one embodiment of the present invention the surface of the PEEK is subjected to a surface treatment to aid adhesion of the second layer and to prevent delaminating and fatigue crack. Suitable surface treatments include but are not limited to chemical etching, abrading, addition of an adhesive, and plasma surface preparations.

In a next step of manufacturing a medical device comprising a microtube, the second layer 120 consisting of a continuous fiber reinforced polymer with continuous reinforced fiber filaments embedded in the polymer matrix in a preferential direction or orientation is then applied over the top of the first layer 110.

In one embodiment of the present invention the second layer 120 consisting of a continuous fiber reinforced polymer is applied over the top of the first layer in a thickness greater than required for the finished sub-assembly. In this embodiment the entire sub-assembly consisting of the two layers is then parallel precision ground across its entire length to a pre defined and optimal outside diameter.

The top layer or third layer 130 may be made from Teflon, ie. PTFE and is applied over the second layer 120 in any thickness desired by for example but not limitation by dipping, spraying, extruding, pultruding, compression molding, or powder coating. In a very preferred embodiment, small uncoated segments 101, 102, and 103 are left uncoated, these small segments representing bonding regions for example but not limited to proximal shaft markers in the appropriate positions 103, or at the ends 101, 102 for attachment of further distal and proximal components, like e.g. a catheter balloon if the medical device comprising this microtube is a balloon dilatation catheter.

In another embodiment of the present invention represented in FIG. 2 the microtube 200 is duallayered. The production thereof is performed using essentially the same techniques as described above. The difference is merely that in this embodiment the inner tube 250 already contains the fiber filaments embedded directly in the PEEK polymer matrix.

As explained in the first embodiment, the top layer or second layer 240 of the microtube 200 of the second embodiment depicted in FIG. 2 may be made from Teflon, ie. PTFE and is applied over the first layer in any thickness desired by for example but not limitation by dipping, spraying, extruding, pultruding, compression molding, or powder coating. In a very preferred embodiment also small uncoated segments 201, 202, and 203 are left uncoated, these small segments representing bonding regions for example but not limited to proximal shaft markers 203 or for further distal or proximal components 201, 202.

The present invention is further directed to the use of a medical device according to the present invention for the treatment of a disease, especially a cardiovascular disease, especially a stenosis.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A medical device comprising a non-metallic microtube, the non-metallic microtube has at least two layers of polymeric material, a first layer of the microtube being made from a Fiber Reinforced Polymer (FRP) comprising a fiber reinforced polyetheretherketone (PEEK), with a layer of fibers being non-continuous, unidirectionally orientated, and disposed in the PEEK, and a second layer being made from polytetrafluroethylene (PTFE), and wherein the non-metallic microtube is not a balloon or an inflatable member and is non-inflatable.

2. The medical device according to claim 1, wherein the non-metallic microtube further comprises PEEK.

3. The medical device according to claim 1, wherein the fibers in the layer of the FRP has unidirectionally orientated fibers in a first direction and the FRP has a second layer of fibers which are unidirectionally orientated in a second direction.

4. The medical device according to claim 1, wherein the non-metallic microtube has at least three layers of different polymeric material, including the inner layer and the outer layer.

5. The medical device according to claim 1, wherein the first layer is made from carbon reinforced PEEK.

6. The medical device of claim 1, further comprising a surface treatment between the inner layer and the outer layer, the surface treatment selected from the group consisting of chemical etching, abrading, addition of an adhesive, and plasma surface treatment.

7. A method of use of a medical device for the treatment of a disease, especially a cardiovascular disease, especially a stenosis, the method comprising:

inserting a medical device into a patient, the medical device comprising a non-metallic microtube, the non-metallic microtube has at least two layers of polymeric material, an inner layer of the microtube being made from a Fiber Reinforced Polymer (FRP) comprising a fiber reinforced polyetheretherketone (PEEK), with a layer of fibers being non-continuous, unidirectionally orientated, and disposed in the PEEK, and an outer layer being made from polytetrafluroethylene (PTFE), and wherein the non-metallic microtube is not a balloon or an inflatable member and is non-inflatable.

8. The method of claim 7, wherein the fibers in the layer of the FRP has unidirectionally orientated fibers in a first direction and the FRP has a second layer of fibers unidirectionally orientated in a second direction.

9. The medical device of claim 7, wherein the short, non-continuous, unidirectionally orientated fibers are carbon fibers.

\* \* \* \* \*